United States Patent [19]

Cassaday et al.

[11] 4,357,301

[45] Nov. 2, 1982

[54] REACTION CUVETTE

[75] Inventors: Michael M. Cassaday, Peekskill, N.Y.; Herman G. Diebler, Redding, Conn.; Dario Svenjak, Fairview, N.J.; Kenneth F. Uffenheimer, Mahopac, N.Y.

[73] Assignee: Technicon Instruments Corp., Tarrytown, N.Y.

[21] Appl. No.: 284,845

[22] Filed: Jul. 20, 1981

[51] Int. Cl.³ .................... G01N 21/03; G01N 21/13
[52] U.S. Cl. .................................. 422/64; 356/246; 422/102
[58] Field of Search .................. 422/61, 64, 57, 58, 422/102; 356/246

[56] References Cited

U.S. PATENT DOCUMENTS

| | | | |
|---|---|---|---|
| 3,504,376 | 3/1970 | Bednar et al. | 422/61 X |
| 3,646,346 | 2/1972 | Catt | 422/57 X |
| 4,088,448 | 5/1978 | Lilja et al. | 422/102 |

*Primary Examiner*—Ronald E. Serwin

[57] ABSTRACT

The reaction cuvette adapted to receive a liquid dispensing probe and having at least one surface of hydrophilic material which is treated or formed to have inwardly extending projections against which the liquid is dispensed.

29 Claims, 12 Drawing Figures

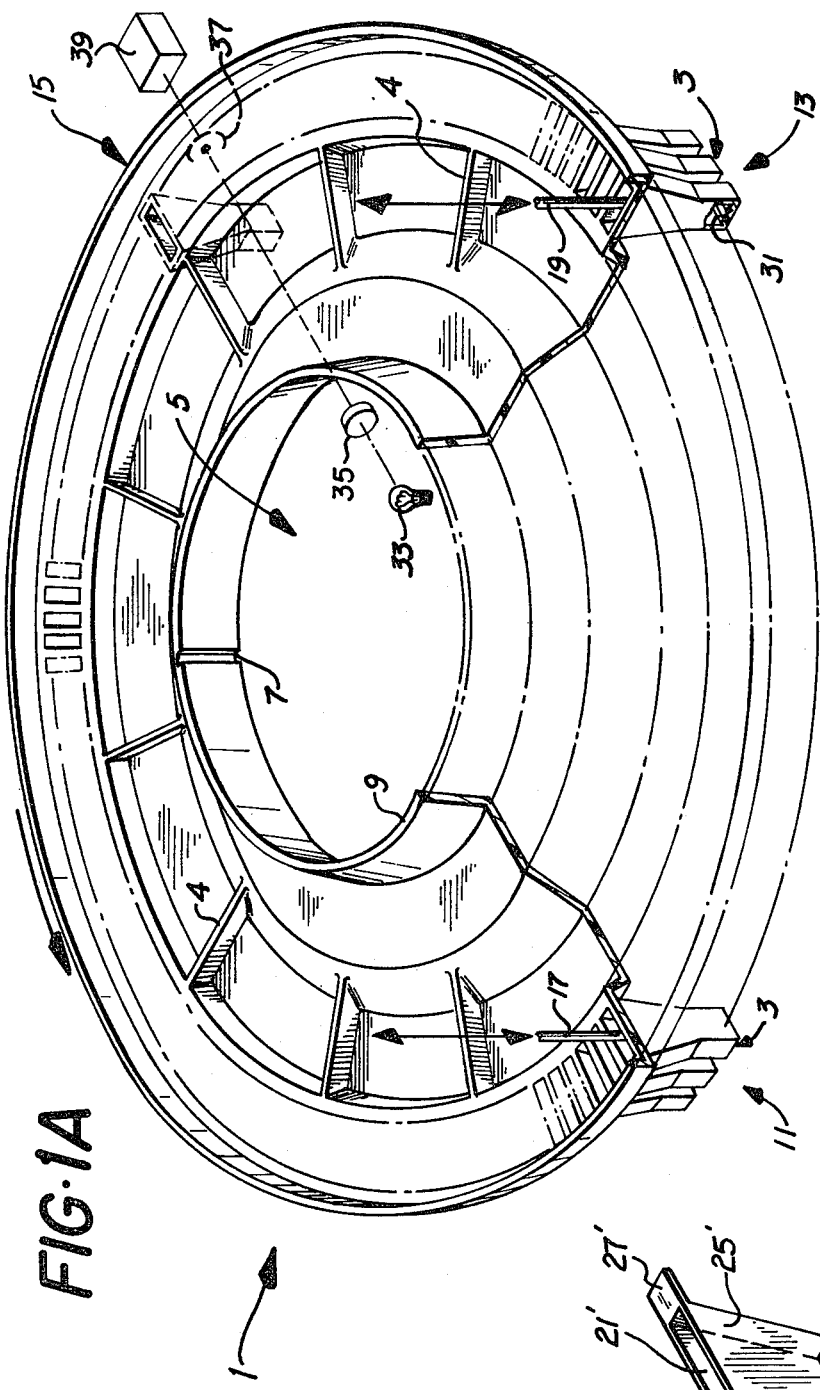
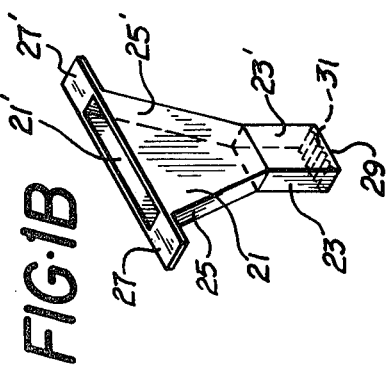
FIG. 1A
FIG. 1B

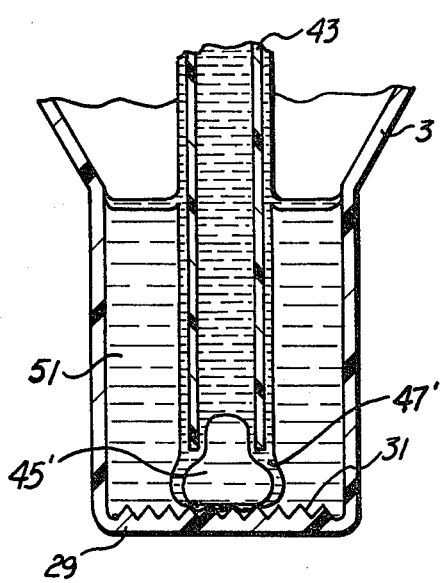
FIG·4A
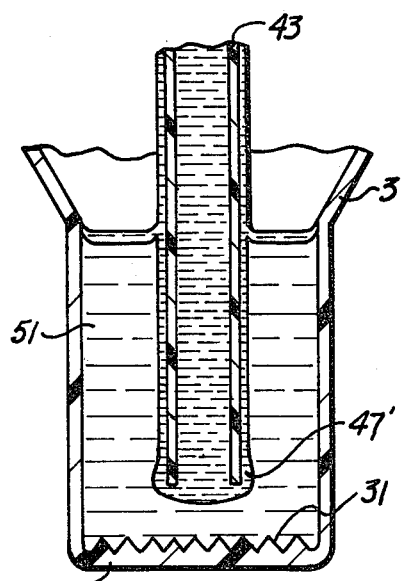
FIG·4B
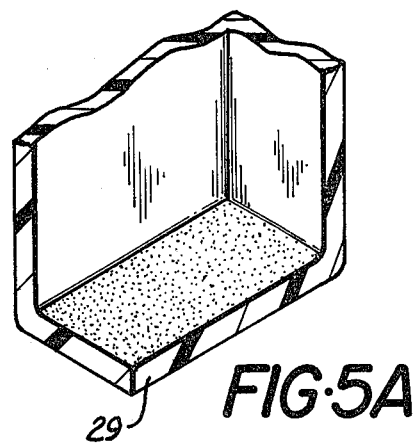
FIG·5A
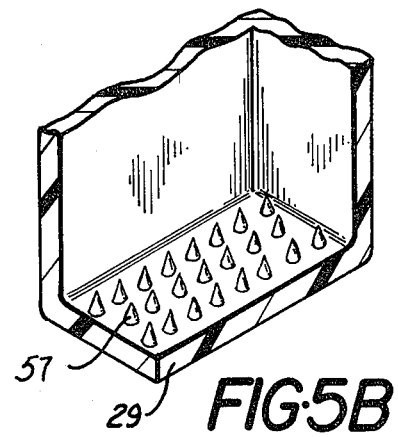
FIG·5B
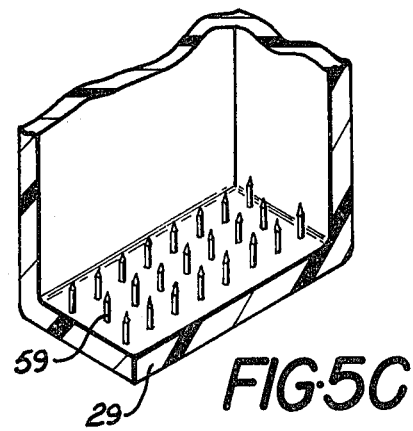
FIG·5C

REACTION CUVETTE

BACKGROUND OF THE INVENTION

1. Field of the Invention

This invention relates to a novel reaction cuvette structure and, more particularly, to a novel reaction tray comprised of a plurality of reaction cuvettes for use in automated analysis systems.

2. Description of the Prior Art

In the field of automated analysis, wherein aqueous samples are reacted in turn in respect of one or more analytes, contamination between successive samples in a major problem. In continuous-flow analytical systems as described in Skeggs et al U.S. Pat. No. 3,241,432, issued on Mar. 22, 1966, and in the Smythe et al U.S. Pat. No. 3,479,141, issued on Nov. 18, 1969, both assigned to a common assignee, sample segments are successively introduced into the system by means of a single aspirating probe, In the Skeggs et al patent, a sequence of air-wash liquid-air segments is aspirated between successive sample segments to substantially reduce contamination therebetween. The sample segments, thus separated, are passed as a continuous stream through the analytical system, so as to be reacted and analyzed in "on-line" fashion. During aspiration of each wash liquid segment, the probe is immersed into the wash liquid reservoir to remove contaminants from or "wash" both interior and exterior probe surfaces. In the latter Smythe et al patent, contamination between successive sample segments in the continuous stream is very substantially reduced by introducing an immiscible liquid, e.g., silicone, fluorocarbon oil, etc., between successive sample segments. The immiscible liquid preferentially wets the interior surfaces of the analytical system, to the complete exclusion of the aqueous sample segments. The sample segments are, in effect, completely encapsulated by the immiscible liquid, whereby contamination between successive sample segments is completely avoided.

Also, in analytical systems which do not utilize continuous-flow techniques, hereafter designated discrete systems, a controlled volume of the aqueous sample and appropriate reagents are precisely metered into a reaction cuvette, the depth of color of the reaction mixture being measured to determine the analyte concentration. Generally, such metering is effected by precisely aspirating a predetermined volume of sample or reagent and dispensing the same into the reaction cuvette. Contaminants and other residues from a previous metering operation are removed from the external probe surface by immersing the probe into a wash-liquid reservoir. Often, the probe is reverse-flushed with an appropriate liquid to clean the interior probe surfaces.

In the A. Reichler et al U.S. Pat. No. 4,121,466, issued on Oct. 24, 1978, and assigned to the common assignee, an improved metering or dispensing system, useful in both continuous-flow and discrete systems, is described, wherein contamination between successively aspirated liquids is completely avoided. In such system, the external and internal probe surfaces which normally contact the aqueous liquids, whether sample or reagent, are continuously coated with a thin film of liquid, which is immiscible with such liquids and preferentially wets such surfaces. Also, the aqueous liquid segments aspirated into the probe for dispensing are completely encapsulated within the immiscible liquid. Hence, the interior and exterior probe surfaces are not in contact with the aqueous liquid during either the aspiration or dispense cycles.

Admittedly, the metering system as described in the aforementioned U.S. Pat. No. 4,121,466 provides very beneficial results in positively eliminating contamination between successively dispensed liquid segments and, also, between sources of different liquids into which the probe is selectively immersed. However, when used as a dispenser in a discrete system, the liquid segments, whether sample or reagent, dispensed into the reaction cuvette may be encapsulated within a film of the immiscible liquid. In certain instances, for example, where a surfactant is present in the liquid being metered, there is a strong tendency for the sample or a portion thereof to remain encapsulated within the immiscible liquid film, which is not easily ruptured during the dispensing cycle. Unless such encapsulating film is ruptured, the dispensed liquid segment is not available for reaction. The present invention is particularly directed to a novel reaction cuvette structure for overcoming such shortcomings of the prior art and positively insuring against the formation of such encapsulating film during the dispensing cycle.

SUMMARY OF THE INVENTION

Accordingly, it is an object of the invention to provide an improved cuvette structure for use in automated analysis systems;

Another object of this invention is to provide a cuvette of improved structure especially in respect to its quality, use facility, quantity-production facility, and production cost;

A further object of this invention is to provide a reaction tray comprising a plurality of cuvettes formed in integral fashion and particularly adapted for use in automated analysis systems;

A still further object of this invention is to provide a novel cuvette structure for use in automated analysis systems, which ensures effective mixing of liquids dispensed into the cuvette.

A further object of this invention is to provide a novel cuvette structure to preclude the formation of and/or insure the rupture of any encapsulating film of immiscible liquid which may be formed during the dispensing cycle of systems such as disclosed in U.S. Pat. No. 4,121,466, supra.

These and other objects and features of this invention are achieved by forming at least one surface of the reaction cuvette, to be particularly adapted to insure a rupturing of the encapsulating immiscible film which may be formed during the dispensing cycle. According to the present invention, the bottom surface of the reaction cuvette is formed of a hydrophilic material and structured to engage with and penetrate the encapsulating immiscible film, so as to rupture the same. In the preferred embodiment, the cuvette bottom defines one or more projections against which the encapsulated liquid segment is positively directed, so as to forcibly penetrate and rupture such encapsulating film. Once penetrated, the surface forces of such encapsulating film are insufficient to maintain the aqueous liquid encapsulate, whereby the aqueous liquid is released and available for reaction.

During the dispensing cycle, the outlet end of the probe is located immediately adjacent the projections on the bottom surface of the reaction curvette. Accordingly, the encapsulating immiscible film, which tends to form a sphere, is dispensed against the bottom surface of the cuvette and deformed against the projections to the point of rupturing. Once ruptured and since inert with respect to the reactants, the immiscible liquid does not interfere with the reaction.

BRIEF DESCRIPTION OF THE DRAWINGS

FIG. 1A is an isometric view of the reaction tray, which is comprised of a plurality of novel reaction cuvettes; FIGS. 1B is an isometric view of one such reaction cuvette;

FIGS. 4A and 4B provide a cross-section view of the reaction cuvette of the present invention; and FIGS. 5A, 5B and 5C are fragmentary views of alternate embodiments of the reaction cuvette of the present invention.

DETAILED DESCRIPTION OF THE INVENTION

Figure 2A:
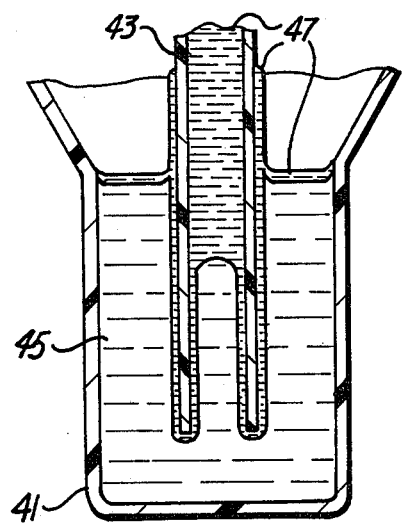
FIGS. 2A and 2B are illustrative of the aspirating cycle and FIGS. 3A, 3B and 3C are illustrative of the dispensing cycle of an aspirating/dispensing probe, such as described in U.S. Pat. No. 4,121,466, supra.

Referring to FIG. 1, the reaction tray 1 of the present invention comprises a plurality of cup-like containers or cuvettes 3, formed in integral fashion and arranged circularly along the periphery of tray 1. Tray 1 is preferably molded of clear acrylic polystyrene or other suitable transparent inert material. Reinforcing ribs 4 provide rigidity to tray 1. Tray 1 is adapted to be mounted through a central opening 5 and keyed by slot 7 to an intermittently rotated shaft, not shown, to rotate about its axis, as indicated by the arrow. A collar 9 is provided which defines slot 7 and facilitates positioning and removal of tray 1 from such shaft. Rotation of such shaft is operative to position each cuvette 3 successively at a reagent dispensing station 11, a sample dispensing station 13, and at an optical readout station 15. As the use of reaction trays in discrete-type analytical systems is well understood and in the interest of expediency, such stations have not been illustrated in detail. Rather, dispensing probes 17 and 19 are shown as symbolic of the reagent and sample dispensing stations, respectively. Probes 17 and 19 are each adapted, as indicated by the arrow, to be displaced vertically, so as to be introduced into and withdrawn from the cuvettes positioned at the reagent and sample dispensing stations 11 and 13, respectively. It will be appreciated that probes 17 and 19, when elevated, are adapted to be rotated in a horizontal plane, so as to be positioned at aspirating stations located over sources of reagent and sample, respectively. When so positioned, the probe 17 would be immersed into such reagent source selectively to aspirate a predetermined volume of reagent which is dispensed into a cuvette 3 located at the dispensing station 11. Also, when such cuvette 3 has been advanced to the sample dispensing station 13, the probe 19 would be immersed into such sample source to aspirate a predetermined volume of sample which is dispensed and reacted in such cuvette. The aspirating and dispensing cycles of probes 17 and 19 are more particularly described hereafter and may take the general form of the aspirator-dispenser unit described in U.S. Pat. No. 4,121,466, supra. Subsequently, the cuvette 3 is advanced to optical readout station 15, whereat the analyte is colorimetrically analyzed, by conventional techniques.

As illustrated in FIGS. 1A and 1B, each cuvette 3 has a substantially rectangular configuration and extends downwardly from the plane of reaction tray 1. Each cuvette 3 includes opposing parallel walls 21 and 21' and 23 and 23', the latter defining tapered portions 25 and 25', respectively. Wall portions 25 and 25' are integral with tab portions 27 and 27', respectively. In the showing of FIG. 1A, tab portions 27 and 27' are integrally defined in tray 1. However, tab portions 27 and 27' would allow support, if cuvette 3 is to be mounted in slots defined in a non-disposable type of turntable. The bottom surface of each cuvette defines a plurality of upwardly extending projections or ribs 31, whose particular function is hereinafter described. Opposing walls 21 and 21' of each cuvette 3 are at a precisely controlled separation. Walls 23 and 23' define a sight path to colorimetrically analyze the reacted sample. When a cuvette 3 is positioned, in turn, at readout station 15, a light beam from source 33 is directed through lense arrangement 35 and along such sight path. The emerging light is incident on detector 37, which produces an output indicative of the concentration of the analyte being measured and which is recorded by recorder 39.

Figure 2B:
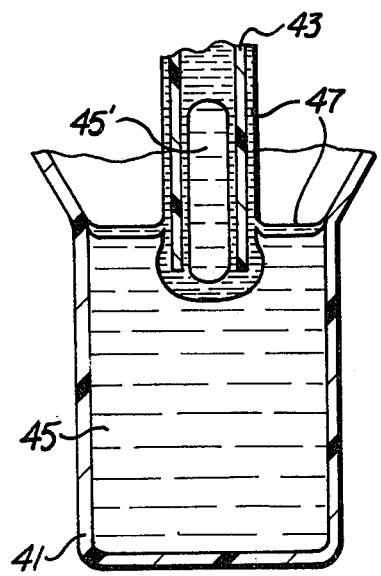

To appreciate the advantages of the present invention, reference is initially made to FIGS. 2A and 2B, which illustrate the aspiration cycles of both probes 17 and 19 of FIG. 1. A container 41 is representative of the reagent source and of sample source into which probes 17 and 19, respectively, of FIG. 1A would be immersed. Also, probe 43 is representative of probes 17 and 19. It will be appreciated that the respective operations of probes 17 and 19 are identical, except in respect of the particular aqueous liquid to be aspirated, i.e., sample or reagent. Conventionally, probe 43 is immersed into container 41 and a controlled negative pressure is applied at the outlet end, as by a pump, to aspirate a controlled volume of the aqueous liquid 45. As particularly described in U.S. Pat. No. 4,212,466, supra, an immiscible fluid 47 is flowed downwardly, at a controlled rate, over outer surface of probe 43 from a chamber, not illustrated, to coat such surface and prevent contact with the liquid to be aspirated. During immersion of probe 43, to effect either an aspirate or dispense operation, the flow of immiscible liquid may be discontinued.

At the beginning of each aspiration cycle, the probe is normally filled with immiscible fluid 47, which serves as pilot fluid to dispense the aspirated liquid segment. To initiate an aspiration cycle, probe 43 is immersed into liquid 45 contained in the vessel. At such time, the flow of externally wetting immiscible fluid 47 is discontinued and liquid 45 is aspirated into the probe, as shown in FIG. 2A. As the immiscible liquid 47 preferentially wets the interior and exterior probe surfaces, to the exclusion of the liquid 45, the aspirated liquid tends to form a discrete segment, which is encased within immiscible liquid and, hence, prevented from contacting the probe surfaces.

During probe immersion, a small portion of excess immiscible fluid 47 is wiped from the outer surface of probe 43, due to the surface tension of liquid 45 and forms a film over the surface of liquid 45 in container 41. As probe 43 is withdrawn, such excess immiscible liquid tends to seal the inlet end of probe 43 and fully encapsulate the aspirated liquid segment 45', as shown in FIG. 2B. Such encapsulation serves, as is known, to prevent contact between liquid segment 45' and the inner surfaces of probe 43, to prevent contamination between successively aspirated liquid segments. Also, the film of immiscible liquid 47 coating the outer surfaces of probe 43 presents contamination between successive liquid sources into which probe 43 may be selectively immersed. It will be appreciated that a number of reagent sources may be provided into which probe 17 of FIG. 1A is selectively immersed, such that sample segments introduced, in turn, into cuvettes 3 at sample dispensing station 13 may be reacted and analyzed for different analytes, on a selective basis.

Figure 3A:
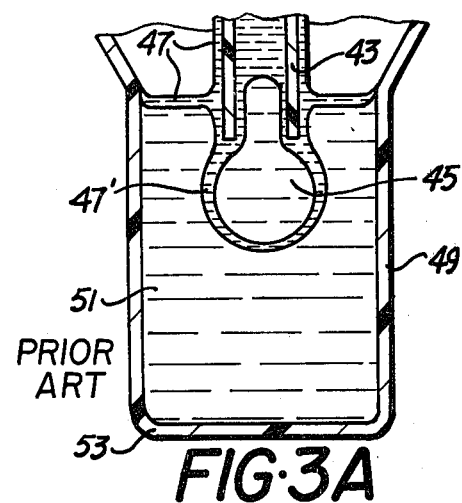
Figure 3B:
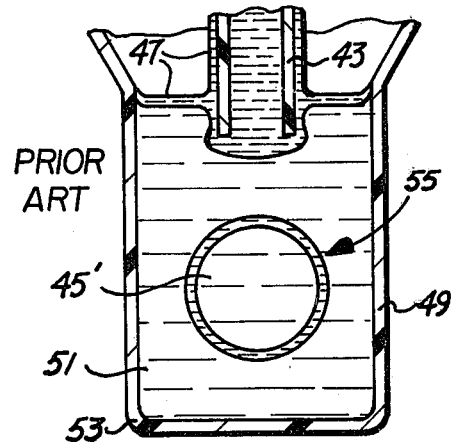
Figure 3C:
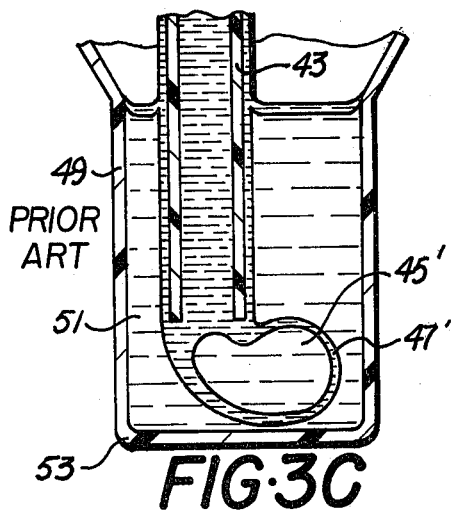

To initiate the dispense cycle, probe 43 is moved to the dispensing station, whether reagent or sample, and positioned over the cuvette 49 located thereat. For purposes of description, FIGS. 3A–3C illustrate a sample dispense station exemplary of the prior art, whereat the cuvette 49 contains a previously dispensed liquid 51, i.e., reagent. As illustrated, cuvette 49 has a planar, substantially smooth bottom 53. Again probe 43 is immersed into cuvette 49, the flow of immiscible liquid 47 over the outer probe surfaces is discontinued and a portion thereof is left behind, to form a film over the surface of liquid 51, as described. At this time, the end of probe 43 is sealed with immiscible fluid 47 and liquid segment 45' remains encapsulated. As liquid segment 45' is dispensed, a portion of immiscible fluid 47 sealing the inlet end of probe 43 forms a thin barrier film 47' which is expanded by the emerging segment, as shown in FIG. 3A. As liquid segment 45' continues to emerge, the barrier film 47' continues to expand and surrounds the liquid segment 45', the surface tensions within both tending toward a spherical or globular shape. When liquid segment 45' has emerged sufficiently from probe 43, as a globule 55, as shown in FIG. 3B. It will be appreciated that, if liquid segment 45' is of considerable size, a series of such globules will be dispensed into cuvette 49. In many instances, the barrier film 47' remains intact, whether dispensed into a liquid medium or into an empty cuvette, whereby the encapsulated liquid segment 45' is unavailable for reaction.

FIG. 3C illustrates the situation where the end of probe 43 is located adjacent to the bottom 53 of cuvette 49. As shown, the emerging liquid segment 45' encapsulated in barrier film 47' is pressed against bottom 53. Because of the smoothness of bottom 53, the encapsulated liquid sample 45' becomes distorted and slips from between the end of probe 43 and bottom 53, as shown, with barrier film 47' intact, such as to form a globule 55, as shown in FIG. 3B.

The novel structure of cuvette 3 insures that the barrier film is prevented from forming a complete encapsulation of the dispensed liquid segment. As shown in FIG. 4A, the bottom 29 of cuvette 3 is provided with one or more upward projections or ridges 31. During the dispensing cycle, the inlet end of probe 43 is located adjacent to bottom 29. The spacing between bottom 29, i.e., ridges 31, and the inlet of probe 43 should be sufficient to prevent buildup of significant back pressure along the probe system during the dispensing cycle, such as not to affect metering, and also be less than the diameter of any globule which might tend to form. During the dispensing operation, the liquid segment 45' encapsulated in barrier layer 47' is compressed against ridges 31. As the liquid segment 45' continues to emerge, the barrier film 47' is forced against the ridges 31, which penetrate and prevent slippage of the barrier layer 47'. As liquid segment 45' continues to emerge from probe 43, such layer is ruptured to release liquid segment 45'. Alternatively, the ridges 31 will ultimately pierce barrier layer 47'. As bottom 29 is formed of hydrophilic material, ridges 31 provide a hydrophilic path or "bridge" accelerating the release of liquid segment 45' to mix with reagent 45 in cuvette 3, as shown in FIG. 4B. Barrier layer 47' would be similarly ruptured, notwithstanding cuvette 3 contains no priorly dispensed liquid, as in the case of the dispensing of reagent at reagent dispensing station 11. Accordingly, the novel cuvette structure insures the availability of the dispensed liquid segment 45', while full advantage is made of the immiscible fluid to prevent contamination, whether between reagent sources into which the probe is selectively immersed or successive sample sources.

While ridges 31 have been shown, it will be appreciated that numerous alternate structures can be utilized to achieve similar results. To obtain advantages of the present invention, the upper surface of bottom 29 should be treated or formed to accelerate rupturing of barrier film 47' by preventing slippage of the emerging globule from between the inlet end of probe 43 and such surface. The bottom surface, for example, may be sandblasted, as shown in FIG. 5A, to insure non-slippage of the emerging globule, the microscopic projections thus defined in the surface serving to penetrate and restrain the barrier film 47'. Also, bottom 29 may be provided with cone-like projections 57, as shown in FIG. 5B, or rod-like projections 59, as shown in FIG. 5C, or any specialized hydrophilic surface designed so as to restrain the emerging globule and provide piercing projections.

What is claimed is:

1. A cup-like receptacle, the interior of said receptacle defining at least one surface which has a plurality of inwardly extending projections of hydrophilic material, said receptacle further defining a sight passageway for analysis of said liquid.

2. A cup-like receptacle as defined in claim 1, wherein said surface defines a plurality of ridge-like projections.

3. A cup-like receptacle as defined in claim 1, wherein said surface defines a plurality of cone-like projections.

4. A cup-like receptacle as defined in claim 1, wherein said surface has been treated as by sandblasting.

5. A cup-like receptacle as defined in claim 1, wherein said receptacle includes at least two parallel transparent opposing wall portions defining said sight passageway.

6. A cup-like receptacle as defined in claim 1, said receptacle adapted to be mounted onto a horizontal support, further including means projecting laterally of said receptacle for supporting said receptacle when mounted on said horizontal support.

7. A cup-like receptacle as defined in claim 6, wherein said receptacle defines two opposing non-parallel wall portions for directing said receptacle when mounting on said support.

8. A cup-like receptacle as defined in claim 1, which is formed of acrylic or polystyrene material.

9. A reaction tray comprising a plurality of reaction cuvettes, said tray adapted to be rotated about an axis, said cuvettes being circularly disposed about said axis, whereby rotation of said tray advances each cuvette, in turn, to a liquid dispensing station, the interior of each cuvette defining at least one surface which has a plurality of inwardly extending projections of hydrophilic material and each of said cuvettes defining a sight passageway for analysis of the contents thereof.

10. The reaction tray of claim 9, wherein said reaction tray defines a central opening for mounting of said tray on a rotatable shaft.

11. The reaction tray of claim 10, wherein said reaction tray includes a structure surrounding said central opening for facilitating mounting of said reaction tray on said shaft.

12. The reaction tray of claim 9, wherein each of said cuvettes is disposed along a radius of said reaction tray.

13. The reaction tray of claim 9, wherein said one surface defines a plurality of ridge-like projections.

14. A reaction tray as defined in claim 9, wherein each of said surfaces defines a plurality of cone-like projections.

15. A reaction tray as defined in claim 9, wherein said surface has been treated as by sandblasting.

16. A reaction tray as defined in claim 9, wherein said tray is formed of acrylic or polystyrene material.

17. A reaction tray as defined in claim 12, wherein each of said cuvettes includes two transparent sides spaced at a predetermined distance to define a sight passageway therethrough, said sight passageway being located along said radius.

18. A reaction tray as defined in claim 9, wherein each of said cuvettes is integrally formed in said reaction tray.

19. The receptacle of claim 1 wherein said one surface forms at least a portion of the bottom of said receptacle.

20. The receptacle of claim 1 which is adapted to receive a probe for dispensing a liquid therein.

21. The receptacle of claim 5 wherein at least the portions of said opposing walls which define said sight passageway have hydrophilic interior surfaces.

22. The receptacle of claim 1 wherein said projections are sharp projections.

23. The receptacle of claim 22 wherein said sharp projections are edged projections.

24. The receptacle of claim 22 wherein said sharp projections are pointed projections.

25. A cup-like receptacle adapted to receive a liquid, which receptacle has a sight passageway for analysis of the contents thereof, and means for rupturing an encapsulated globule of said liquid received therein.

26. The receptacle of claim 25 wherein said rupturing means comprises means for rupturing an immiscible liquid encapsulated globule of said liquid received therein.

27. The receptacle of claim 25 wherein said rupturing means comprises a plurality of inwardly extending projections of hydrophilic material.

28. A reaction tray comprising a plurality of reaction cuvettes, said tray adapted to be moved relative to a liquid dispensing station to successively advance each cuvette to said liquid dispensing station, wherein each cuvette has a sight passageway for analysis of the contents thereof, and means for rupturing an immiscible liquid encapsulated globule of said liquid.

29. The reaction tray of claim 28 wherein the rupturing means of each cuvette comprises a plurality of inwardly extending projections of hydrophilic material.

* * * * *